US00PP11749P2

(12) United States Plant Patent
Cain

(10) Patent No.: US PP11,749 P2
(45) Date of Patent: Jan. 23, 2001

(54) GRAPE PLANT NAMED 'SUGRASIXTEEN'

(75) Inventor: David W. Cain, Bakersfield, CA (US)

(73) Assignee: Sun World International, Inc., Bakersfield, CA (US)

( * ) Notice: Under 35 U.S.C. 154(b), the term of this patent shall be extended for 0 days.

(21) Appl. No.: 09/196,841

(22) Filed: Nov. 20, 1998

(51) Int. Cl.[7] ..... A01H 5/00
(52) U.S. Cl. ..... Plt./205
(58) Field of Search ..... Plt./206, 205

(56) References Cited

U.S. PATENT DOCUMENTS

P.P. 3,106 4/1972 Garabedian .
P.P. 4,787 11/1981 Olmo et al. .

*Primary Examiner*—Howard J. Locker
*Assistant Examiner*—Melissa L. Kimball
(74) *Attorney, Agent, or Firm*—Knobbe, Martens, Olson & Bear, LLP

(57) ABSTRACT

A new and distinct grapevine variety characterized by its black seedless berries that ripen in mid season and have a unique, fruity, muscat-type flavor; juicy, moderately firm flesh; and tough skin. The berries of the new variety are borne upon very strong woody stems which are well adapted to commercial handling.

1 Drawing Sheet

BACKGROUND AND SUMMARY OF THE INVENTION

This invention relates to the discovery and asexual propagation of a new variety of grapevine, *Vitis vinifera* cv. 'Sugrasixteen' . The new variety was first hybridized by David W. Cain in Wasco, Kern County, Calif., the variety being originated by controlled hybridization and subsequent ovule culture of normally abortive seeds. The new variety is characterized by producing black grapes having very small, vestigial seed traces that are not noticeable when eaten. The new variety is highly productive and may be spur pruned to two bud spurs.

The seed parent is the 'Black Monukka' variety (unpatented) and the pollen parent is 'Sugrafive' (U.S. Plant Pat. No. 5,151). The parent varieties were first crossed in May, 1988, with the date of first flowering being May, 1991. The new 'Sugrasixteen' variety was first asexually propagated by David W. Cain in December, 1991 in Wasco, Kern County, Calif., using cuttings.

The new grapevine variety cv. 'Sugrasixteen' most nearly resembles its seed parent the 'Black Monukka'. It differs from the 'Black Monukka' by ripening approximately 7 days earlier, by having firmer flesh and tougher skin, by having a much smaller and less lignified seed, and by possessing a distinct vinous muscat flavor.

'Sugrasixteen' is distinguished from other commonly grown black seedless grapes such as the 'Beauty Seedless' (unpatented), 'Fantasy' (unpatented), 'Larson B-36' (U.S. Plant Pat. No. 9,039), 'Mariah' (U.S. Plant Pat. No. 9,040), and 'Marroo' (U.S. Plant Pat. No. 7,377) by possessing a highly desirable, strong, distinct, vinous, fruity flavor most nearly similar to that commonly referred to as muscat but differing from the flavor of commonly known muscat grapes such as the 'Muscat of Alexandria,' 'Muscat Hamburg,' and 'Italia' varieties (all unpatented).

The new variety further can be distinguished from the above cited varieties by possessing a much thicker, stronger and more highly lignified rachis which provides superior handling characteristics during commercial harvesting and shipping procedures. The region of the peduncle most proximal to the cane often becomes brown and woody while the peduncles of the above cited varieties most often remain green and less woody than the new variety.

The new variety ripens later than the 'Beauty Seedless,' 'Larson B-36,' and 'Mariah' varieties and ripens more nearly with the 'Fantasy' and 'Marroo' varieties. It is moderately responsive to gibberellic acid applications to reduce berry number and to increase berry size, but high levels induce phytotoxicity and increase berry shatter during harvest shipping.

The new 'Sugrasixteen' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
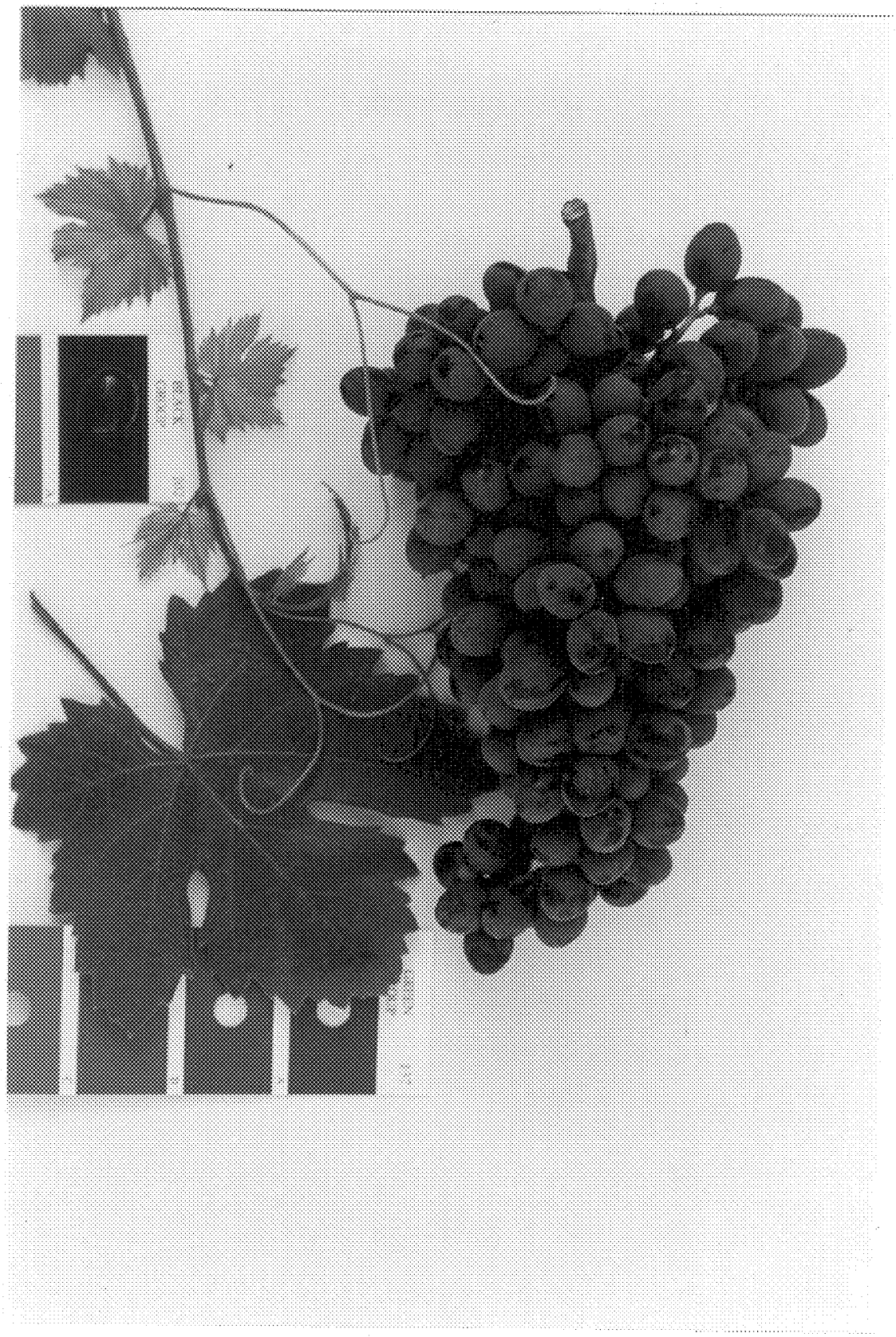

Throughout this specification, color names beginning with a small letter signify that the name of that color, as used in common speech, is aptly discriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrasixteen' plants grown in the vicinity of Wasco, Kern County, Calif., during 1998, and is believed to apply to plants of the variety grown under similar conditions of soil and climate elsewhere:

VINE

General:
*Size*.—Large.
*Vigor*.—Medium.
*Density of foliage*.—Dense.
*Productivity*.—Productive when spur pruned, up to 28.3 kg/vine.
*Root stock*.—Own root.
Truck:
*Shape*.—Medium.
*Straps*.—Long, split.
*Surface texture*.—Shaggy.
*Inner bark color*.—About Greyed-Orange 176D.

SHOOTS

Young shoot:
*Form of tip*.—Half-open.
*Distribution of anthocyanin coloration of tip*.—Absent.
*Intensity of anthocyanin coloration of tip*.—Absent.
*Density of prostrate hairs on tip*.—Medium to dense.
*Density of erect hairs on tip*.—Absent to very sparse.
Flowering shoot:
*Vigor during flowering*.—Strong.
*Attitude during flowering on shoots which are not tied*.—Semi-drooping.
*Color of dorsal side of internodes*.—About Yellow-Green 144B with Greyed-Purple 183B stripes.
*Color of ventral side of internodes*.—About Yellow-Green 144B with Greyed-Purple 183B stripes.
*Color of dorsal side of nodes*.—About Yellow-Green 144B with Greyed-Purple 183B stripes.
*Color of ventral side of nodes*.—About Yellow-Green 144B.
*Erect hairs on nodes*.—None.
*Erect hairs on internode*.—Absent.
*Prostrate hairs on nodes*.—None.
*Prostrate hairs on internodes*.—Absent.
*Anthocyanin coloration of buds*.—Weak.
Tendrils:
*Distribution on the shoot at full flowering*.—Discontinuous.
*Thickness*.—Thin.
*Color*.—About Yellow-Green 145A.
*Form*.—Bifurcated or occasionally trifurcated.
*Number of consecutive tendrils*.—Up to two.
*Length of tendril*.—Long, about 28.8 cm.

LEAVES

Young leaves:
*Color of upper surface of first 4 distal unfolded leaves*.—About Green 143A.
*Average intensity of anthocyanin coloration of six distal leaves prior to flowering*.—Absent.
*Density of prostrate hairs between veins at lower surface of 4th distal unfolded leaf*.—Absent or very sparse.
*Erect hairs between veins at lower surface of 4th distal unfolded leaf*.—Absent.
*Density of prostrate hairs on veins at lower surface of 4th distal unfolded leaf*.—Very sparse.
*Density of erect hairs on veins at lower surface of 4th distal unfolded leaf*.—Very sparse.

Mature leaves:
*Average length*.—About 16.6 cm.
*Average width*.—About 19.6 cm.
*Size of blade*.—Medium to large.
*Shape of blade*.—Pentagonal.
*Number of lobes*.—3.
*Anthocyanin coloration of main veins on the upper side of the blade*.—Weak.
*Mature leaf profile*.—Involute.
*Blistering surface of blade upper surface*.—Medium to strong.
*Leaf blade tip*.—In the plane of the leaf.
*Undulation of margin*.—Pronounced.
*Apex*.—Cuspidate.
*Thickness*.—Medium.
*Undulation of blade between main and lateral veins*.—Absent.
*Shape of teeth*.—Both sides convex.
*Length of teeth*.—Medium.
*Ratio length/width of teeth*.—Medium.
*General shape of petiole sinus*.—Slightly open to closed.
*Tooth at petiole sinus*.—Absent.
*Petiole sinus limited by veins*.—Absent.
*Shape of upper lateral sinus*.—Lobes slightly overlapping.
*Depth of upper lateral sinus*.—Shallow.
*Prostrate hairs between veins on lower surface of blade*.—Absent.
*Erect hairs between veins on lower surface of blade*.—Absent.
*Prostrate hairs on main veins on lower surface of blade*.—None.
*Density of erect hairs on main veins on lower surface of blade*.—None or very sparse.
*Prostrate hairs on mains vein on upper surface of blade*.—Absent.
*Autumn coloration of leaves*.—About Greyed-Purple 187A.
Upper surface:
*Color*.—About Green 137A.
*Surface texture*.—Rugose.
*Surface appearance*.—Semi-glossy.
*Goffering of blade*.—Absent.
Lower surface:
*Color*.—About Green 137C.
*Anthocyanin coloration of main veins on lower leaf surface*.—Absent.
*Glossiness*.—Medium.
*Pubescence*.—Absent.
*Surface texture*.—Smooth.
*Surface appearance*.—Semi-glossy.
Petiole:
*Length of petiole*.—Long, about 14.0 cm.
*Length of petiole compared to middle vein*.—Equal to slightly longer.
*Density of prostrate hairs on petiole*.—None.
*Density of erect hairs on petiole*.—None.
*Shape of base of petiole sinus*.—V-shaped.
Woody shoot:
*Shape*.—Stocky.
*Internode length*.—Medium, about 121.3 mm.
*Width at node*.—About 21.7 mm.
*Cross section*. —Elliptic.
*Surface*.—Smooth.
*Main color*.—About Greyed-Orange 165D.

*Lenticels*.—Inconspicuous.
*Density of erect hairs on nodes*.—None.
*Density of erect hairs on internodes*.—None.
*Growth of axillary shoots*.—Medium, about 54.8 cm.

Buds:
*Shape*.—Slightly pointed.
*Size*.—Medium, about 6.5×6.9 mm (length×width).
*Position*. —Markedly held out, about 50° angle.
*Cane bud fruitfulness*.—Basal most fruitful.
*Time of bud burst*.—Medium.

FLOWERS

General:
*Flower sex*.—Perfect.
*Length of first inflorescence*.—Long, about 270 cm.
*Position of first flowering nodes*.—3rd to 4th.
*Number of inflorescences per shoot*.—1.1 to 2.
*Date of full bloom*.—May 20, 1998.
*Time of bloom*.—Medium, as compared with similar varieties in the growing area of Wasco, Kern County, Calif.
*Duration of bloom period*.—Average, about 10 days.
*Size* (*diameter of fully open flower*).—Medium.
*Color*.—About Yellow-Green, 145A.

FRUIT

General:
*Ripening period*.—Medium; about 10 days before the 'Thompson Seedless' variety.
*Date of ripening*.—About July 20; varies from July 4 to August 5, depending upon the year.
*Use*.—Fresh market.
*Keeping quality*.—Medium.
*Resistance*.—Insects: typical of *Vitis vinifera*. Diseases: typical of *Vitis vinifera*.
*Shipping quality*.—Medium.
*Date of first harvest*.—Jul. 15, 1998.
*Solids-sugar*.—High (~21%).
*Refractometer test*.—About 20.2° brix.
*Acid*.—Very low, about 0.45 g/L tartaric acid.
*Juice pH*.—4.32.

Cluster:
*Bunch size* (*peduncle excluded*).—Large.
*Bunch length* (*peduncle excluded*).—*Long, about* 23.2 cm.
*Bunch width*.—About 17.7 cm.
*Bunch weight*.—High, about 709.1 g (average).
*Bunch density*.—Very dense.
*Number of berries*.—About 222.
*Form*.—Conical.

Penduncle:
*Length of peduncle*.—Short, about 6.0 cm.
*Lignification of peduncle*.—Strong.
*Color*.—About Yellow-Green 144B.

Berry:
*Size*.—Medium.
*Uniformity of size*.—Uniform.
*Berry weight*.—Medium, about 3.42 g.
*Shape*.—Ovate to obtuse ovate.
*Presence of seeds*.—Rudimentary, about 6.1 mg/seed fresh weight.
*Cross section*.—Circular.
*Dimensions*.—Longitudinal axis about 19.7 mm; horizontal axis about 18.0 mm.
*Skin color* (*without bloom*).—About Black 202A.
*Coloration of flesh*.—Clear.
*Juiciness of flesh*.—Very juicy.
*Berry firmness*.—Medium.
*Paticular flavor*.—Strong, fruity, unusual muscat.
*Bloom* (*cuticular wax*).—Strong.
*Pedicel length*.—Intermediate, about 6.7 mm.
*Berry separation from pedicel*.—Difficult.
*Visibility of hilum*.—Unclear.
*Torus*.—Medium large.

Skin:
*Thickness*.—Thick.
*Texture*.—Tough.
*Reticulation*.—Absent.
*Roughness*.—Absent.
*Tenacity*.—Tenacious to flesh.
*Tendency to crack*.—Highly resistant.

What is claimed is:

1. A new and distinct variety of grapevine cv. 'Sugrasixteen' as herein illustrated and described.

* * * * *